(12) United States Patent
Lim et al.

(10) Patent No.: US 10,064,951 B2
(45) Date of Patent: Sep. 4, 2018

(54) LIQUID FORMULATION OF HIGHLY CONCENTRATED LONG-ACTING HUMAN GROWTH HORMONE CONJUGATE

(71) Applicant: HANMI SCIENCE CO., LTD, Hwaseong-si, Gyeonggi-do (KR)

(72) Inventors: Hyung Kyu Lim, Hwaseong-si (KR); Hyun Uk Kim, Busan (KR); Sung Hee Hong, Suwon-si (KR); Sung Min Bae, Seongnam-si (KR); Se Chang Kwon, Seoul (KR)

(73) Assignee: HANMI SCIENCE CO., LTD., Hwaseong-si (KR)

( * ) Notice: Subject to any disclaimer, the term of this patent is extended or adjusted under 35 U.S.C. 154(b) by 0 days.

(21) Appl. No.: 14/383,820

(22) PCT Filed: Mar. 23, 2013

(86) PCT No.: PCT/KR2013/002660
§ 371 (c)(1),
(2) Date: Sep. 8, 2014

(87) PCT Pub. No.: WO2013/147559
PCT Pub. Date: Oct. 3, 2013

(65) Prior Publication Data
US 2015/0118255 A1    Apr. 30, 2015

(30) Foreign Application Priority Data

Mar. 30, 2012 (KR) .......................... 10-2012-0033580

(51) Int. Cl.

| | | |
|---|---|---|
| *A61K 47/02* | (2006.01) | |
| *A61K 47/10* | (2017.01) | |
| *A61K 47/12* | (2006.01) | |
| *A61K 47/20* | (2006.01) | |
| *A61K 47/68* | (2017.01) | |
| *A61K 47/26* | (2006.01) | |
| *C07K 14/61* | (2006.01) | |
| *A61K 47/48* | (2006.01) | |
| *A61K 38/27* | (2006.01) | |
| *A61K 9/08* | (2006.01) | |
| *A61K 9/00* | (2006.01) | |

(52) U.S. Cl.
CPC ...... *A61K 47/48369* (2013.01); *A61K 9/0019* (2013.01); *A61K 9/08* (2013.01); *A61K 38/27* (2013.01); *A61K 47/02* (2013.01); *A61K 47/10* (2013.01); *A61K 47/12* (2013.01); *A61K 47/26* (2013.01); *A61K 47/68* (2017.08); *A61K 47/6811* (2017.08); *C07K 14/61* (2013.01); *C07K 2319/30* (2013.01)

(58) Field of Classification Search
None
See application file for complete search history.

(56) References Cited

U.S. PATENT DOCUMENTS

| | | | | |
|---|---|---|---|---|
| 5,045,312 A | | 9/1991 | Aston et al. | |
| 5,374,620 A | * | 12/1994 | Clark | A61K 9/0019 514/11.3 |
| 5,763,394 A | * | 6/1998 | O'Connor | A61K 9/0019 514/11.3 |
| 5,981,485 A | * | 11/1999 | O'Connor | A61K 9/0019 514/11.3 |
| 7,001,892 B1 | * | 2/2006 | Chmielewski | A61K 31/7016 514/53 |
| 7,608,270 B2 | * | 10/2009 | Beckett | A61K 36/06 424/195.15 |
| 7,736,653 B2 | * | 6/2010 | Kim et al. | 424/178.1 |
| 7,790,679 B2 | * | 9/2010 | Li et al. | 514/7.7 |
| 8,338,374 B2 | * | 12/2012 | Wadhwa et al. | 514/11.4 |
| 2005/0059129 A1 | | 3/2005 | Park | |

FOREIGN PATENT DOCUMENTS

| | | | |
|---|---|---|---|
| EP | 0 413 622 A1 | 2/1991 | |
| JP | 6508156 A | 9/1994 | |
| KR | 10-0567902 B1 | 4/2006 | |
| KR | 10-0725315 B1 | 6/2007 | |
| KR | 10-2008-0041661 A | 5/2008 | |
| WO | 93/15199 A1 | 8/1993 | |
| WO | 93/15200 A1 | 8/1993 | |
| WO | 93/19776 A1 | 10/1993 | |
| WO | 94/03198 A1 | 2/1994 | |
| WO | WO94/03198 * | 2/1994 | ............. A61K 37/02 |
| WO | 96/32478 A1 | 10/1996 | |
| WO | WO97/29767 * | 8/1997 | ............. A61K 38/27 |

(Continued)

OTHER PUBLICATIONS

Machine translation of Korean patent Application 10-2003-0061434, published Mar. 10, 2005.*
Bis et al., Role of Benzyl Alcohol in the unfolding and aggregation of Interferon α-2a. J. Pharm. Sci., 104, 407-415, 2015.*
Ross Clark, et al., "Long-acting Growth Hormones Produced by Conjugation with Polyethylene Glycol," The Journal of Biological Chemistry, Sep. 6, 1996, pp. 21969-21977, vol. 271, No. 36.
Cynthia Bosquillon, et al., "Pulmonary delivery of growth hormone using dry powders and visualization of its local fate in rats," Journal of Controlled Release, 2004, pp. 233-244, vol. 96, No. 2.
George N. Cox, et al., "A Long-Acting, Mono-PEGylated Human Growth Hormone Analog Is a Potent Stimulator of Weight Gain and Bone Growth in Hypophysectomized Rats," Endocrinology, 2007, pp. 1590-1597, vol. 148, No. 4.

(Continued)

*Primary Examiner* — Elly-Gerald Stoica
(74) *Attorney, Agent, or Firm* — Sughrue Mion, PLLC (57) ABSTRACT

The present invention relates to a liquid formulation of highly concentrated long-acting human growth hormone conjugate, comprising a pharmaceutically effective amount of the long-acting human growth hormone conjugate in which human growth hormone (hGH) is linked to an immunoglobulin Fc region, and an albumin-free stabilizer, said stabilizer comprising a buffer, a non-ionic surfactant, a sugar alcohol, and sodium chloride as an isotonic agent, and a method for preparing the same.

18 Claims, 2 Drawing Sheets

(56) References Cited

FOREIGN PATENT DOCUMENTS

| WO | 97/34631 A1 | | 9/1997 | |
|---|---|---|---|---|
| WO | WO2011/015649 | * | 2/2011 | ............. A61K 47/48 |
| WO | 2012/008779 A2 | | 1/2012 | |
| WO | WO2012008779 | * | 1/2012 | ............... A61K 9/08 |

OTHER PUBLICATIONS

International Searching Authority, International Search Report of PCT/KR2013/002660 dated Jul. 4, 2013.
International Searching Authority, Written Opinion of PCT/KR2013/002660 dated Jul. 4, 2013.
Japan Patent Office; Communication dated Jan. 4, 2017 in counterpart application No. 2015-503126.
Taiwanese Patent Office; Communication dated Oct. 25, 2016, in counterpart application No. 102111362.

* cited by examiner

LIQUID FORMULATION OF HIGHLY CONCENTRATED LONG-ACTING HUMAN GROWTH HORMONE CONJUGATE

CROSS REFERENCE TO RELATED APPLICATIONS

This is a National Stage of International Application No. PCT/KR2013/002660 filed Mar. 29, 2013, claiming priority based on Korean Patent Application No. 10-2012-0033580 filed Mar. 30, 2012, the contents of all of which are incorporated herein by reference in their entirety.

TECHNICAL FIELD

The present invention relates to a liquid formulation of highly concentrated long-acting human growth hormone conjugate, comprising a pharmaceutically effective amount of the long-acting human growth hormone conjugate in which human growth hormone (hGH) is linked to an immunoglobulin Fc region, and an albumin-free stabilizer, said stabilizer comprising a buffer, a non-ionic surfactant, a sugar alcohol, and sodium chloride as an isotonic agent, and a method for preparing the same.

BACKGROUND ART

Human growth hormone (hereinafter referred to as 'hGH') is a polypeptide hormone consisting of 191 amino acids having a molecular weight of about 22,000 Da being secreted from the anterior pituitary gland. A human growth hormone has been used for the treatment of pediatric pituitary dwarfism mostly. Previously, hGH extracted from human pituitary gland was used, but its supply is limited. Thus only very limited number of people could be treated. Also, after the incidence of degenerative neurological disorder Creutzfeldt-Jacob disease was reported for some of the patients who received the hGH collected from pituitary gland, a use of hGH extracted from pituitary glands has been banned. Currently with the development of genetic engineering techniques, production of hGH in *E. coli* and yeast has become possible. Thus the biosynthetic hGH medicines produced by genetic engineering have become commercially available through passing toxicological and clinical tests and being approved in several countries after 1985.

In general, polypeptides like hGH have a low stability and thus easily denatures. Also they are readily degraded by serum proteases and removed by kidney or liver. Thus, protein drugs containing polypeptides as pharmaceutical ingredient have to be frequently administered to patients in order to maintain its blood concentration and titer. However, since the protein drugs are often administered in a form of injection, frequent injection of protein drugs to maintain the optimal blood concentration of active polypeptides causes a lot of pain to patients. To solve these problems, there have been many attempts to increase the stability of protein drug in blood and maintain its blood concentration at high level for a long period of time in order to maximize the therapeutic effects of medicine. For the development of a long-acting formulation of the protein drug, one has to make sure that the formulation increases the stability of protein drug while maintaining sufficiently high titer of the drug itself, without causing any immune response in patients.

As a method to stabilize proteins and prevent them from contacting protease and renal loss, a highly soluble polymer such as polyethylene glycol (PEG) has been chemically added to surface of protein drugs. PEG binds to a specific site of a target protein or various sites non-specifically and increases the protein solubility, thereby stabilizing the protein. Also, PEG is effective in prevention of hydrolysis of protein and does not cause any particular side-effects. Although PEG binding may increase the protein stability, a titer of physiologically active protein becomes significantly low, and as the molecular weight of PEG increases, its reactivity with protein is reduced, thereby reducing a yield.

As an alternative method for increasing in vivo stability of physiologically active proteins, a method of producing fusion protein has been developed by connecting a gene encoding for protein with high stability in blood and a gene for physiologically active protein through genetic recombination and culturing the animal cells that are transformed with the recombinant genes. For instance, albumin or its fragment that are known to be highly effective in increasing protein stability can be linked to a targeted physiologically active protein through gene recombination for producing a fusion protein (International Patent Publication Nos. WO 93/15199 and WO 93/15200, European Patent Publication No. EP 413,622).

In addition, as a method for using immunoglobulin, U.S. Pat. No. 5,045,312 discloses that when hGH is conjugated with bovine serum albumin (BSA) or murine immunoglobulin by using a cross-linking agent, activity of the conjugated hGH is increased compared to the unmodified growth hormone. However, the above patent only discloses low-molecular weight compounds such as carbodiimide or glutaraldehyde as a cross-linking agent. When these low-molecular weight cross-linking agents are used, it is hard to obtain homogeneous compositions due to non-specific conjugation, and it may be toxic in vivo. Further, the above-referenced patent merely discloses the increase of growth hormone activity by chemical coupling, but did not describe the effect of chemical coupling on the activity of other types of polypeptide drugs, with no understanding of the correlation with the stability of proteins such as the increase in durability and serum half-life.

Recently, Korean Patent No. 10-0567902 (Physiologically Active Polypeptide Conjugate Having Improved In Vivo Durability) and Korean Patent No. 10-0725315 (Protein Complex Using An Immunoglobulin Fragment And Method For The Preparation Thereof) disclose conjugates prepared by linking physiologically active polypeptides with an immunoglobulin Fc region and a non-peptide polymer, as long-acting formulations of protein drugs which allow for both a minimal reduction of protein activity and an increase in protein stability. According to these methods, hGH may be used as a physiologically active polypeptide to prepare a long-acting hGH conjugate. For commercializing the drug containing long-acting hGH conjugates, it is essential to prevent physicochemical changes such as denaturation, aggregation, adsorption, or hydrolysis due to degradation induced by light, heat or impurities in additives during a storage and transport process, while retaining in vivo effect of hGH. Compared to a hGH polypeptide, a long-acting hGH conjugate has a larger size and increased molecular weight, and thus there is a difficulty in stabilizing the conjugate.

In a pharmaceutical industry, low protein stability in liquid has been a limitation. Thus proteins have been freeze-dried to solve the stability issue. Although a freeze-dried protein formulation has an advantage of retaining stability for a long period of time, when injected it has to be reformulated with dissolution aids. Also, when it is reformulated with dissolution aid or freeze-dried, there were disadvantages in that its activity is often lost due to formation of polymers etc, and the cost and time required for freeze-drying process was high as well. In order to overcome these limitations, International Patent Publication No. WO93/019776 and No. WO94/003198 disclose a stable liquid formulation of hGH. For development of a stable liquid hGH formulation, it is important to control the degradation of hGH such as regulation of production rate of degradation products from deamidation, polymer formation, and oxidation process. Temperature, pH, and additives of liquid formulation affect the production rate of the degradation product, but the formulation that can stabilize all types of proteins allowing for its clinical application has not been known yet. Furthermore, the liquid formulation that has a stabilizing effect for specific protein is often not applicable for stabilization of other proteins. In this regard, the above references disclose that it is first required to perform the selection and combination of factors and additives that can minimize the production rate of specific degradation product of protein in a broad manner to maximize the stability of hGH protein in liquid.

Furthermore, different proteins may be gradually inactivated under different ratio and conditions during storage due to difference in their chemical properties. That is, effects of a stabilizer for extending the storage period are not the same for different proteins. For this reason, the stabilizers used for storage stability have various suitable ratio, concentration, and types according to the physicochemical properties of a target protein. However, when different stabilizers are used simultaneously, it may cause contrary results due to competitive interaction between them and side effects. Furthermore, as properties and concentration of the stored protein may change during its storage, the stabilizers may show different effects from expected. Thus, stabilization of protein in solution takes a lot of efforts and cautions.

Particularly, since long-acting hGH conjugates with increased in vivo durability and stability are prepared by linking a physiologically active peptide hGH with immunoglobulin Fc regions and have significantly different molecular weight and volume from other typical hGH, they require special composition for stabilizing the protein. Also, each of the physiologically active peptide hGH and immunoglobulin Fc region has different physicochemical properties, they both need to be stabilized simultaneously. However, as described above, different peptides or proteins may be gradually inactivated under different ratio and conditions during storage due to the difference in their physicochemical properties. Also, when stabilizers suitable for each peptide or protein are used simultaneously, it may cause contrary results due to competitive interaction between them and side effects. Furthermore, as properties and concentration of the stored protein may change during its storage, the stabilizers may show different effects from expected. Therefore, for a long-acting hGH conjugate, it is difficult to find a stabilizer formulation that can stabilize both of a physiologically active peptide hGH and immunoglobulin Fc region simultaneously.

DISCLOSURE

Technical Problem

In an effort to find a composition for increasing the stability of a liquid formulation of highly concentrated long-acting human growth hormone conjugate such that it can be stored for a long period of time without concerning about viral contamination and for reducing protein precipitation, the present inventors have found that when a stabilizer comprising a buffer, a sugar alcohol, a non-ionic surfactant, and sodium chloride as an isotonic agent is used, the stability of a highly concentrated long-acting hGH conjugate was increased, and thus a cost-effective and stable liquid formulation could be prepared. Also, it was confirmed that even with the addition of preservative, the highly concentrated long-acting hGH conjugate could be stably stored, thereby completing the present invention.

Technical Solution

One object of the present invention is to provide a liquid formulation of highly concentrated long-acting human growth hormone conjugate, comprising a pharmaceutically effective amount of the long-acting human growth hormone conjugate in which human growth hormone (hGH) is linked to an immunoglobulin Fc region, and an albumin-free stabilizer, said stabilizer comprising a buffer, a non-ionic surfactant, a sugar alcohol and sodium chloride as an isotonic agent.

Another object of the present invention is to provide a method for preparing the liquid formulation of highly concentrated long-acting human growth hormone conjugate.

Advantageous Effects

The liquid formulation of highly concentrated long-acting hGH conjugate of the present invention comprises a stabilizer that contains a buffer, a sugar alcohol, a non-ionic surfactant, and sodium chloride as an isotonic agent, but does not have a human serum albumin and any potentially hazardous factors for body. Thus, there is no concern of viral contamination. In addition, the present formulation allows for a high stability in the long-acting hGH conjugate which is prepared by linking hGH polypeptide and immunoglobulin Fc region, thereby having a larger molecular weight compared to a wild-type and increased in vivo durability. Also, the liquid formulation is stable even when it further comprises preservative, and thus can be used as a formulation for multiple administration.

BEST MODE

In one embodiment, the present invention provides a liquid formulation of highly concentrated long-acting human growth hormone conjugate, comprising a pharmaceutically effective amount of the long-acting human growth hormone conjugate in which human growth hormone (hGH) is linked to an immunoglobulin Fc region, and an albumin-free stabilizer, said stabilizer comprising a buffer, a non-ionic surfactant, a sugar alcohol and sodium chloride as an isotonic agent.

The liquid formulation of highly concentrated long-acting hGH conjugate of the present invention comprises an albumin-free stabilizer, which ensures a stability of the long-acting hGH conjugate without a risk of viral contamination. In addition, it is a simple formulation having excellent storage stability, and thus it allows for more cost-effective provision of drugs compared to other stabilizers or freeze-dried formulation. Also, since the liquid formulation of the present invention comprises the long-acting hGH conjugate which has increased in vivo durability compared to a wild-type protein, it can retain a protein activity in vivo for a long period of time compared to other common hGH formulation, and thus it can be used as an efficient drug formulation that ensures a high stability of highly concentrated long-acting hGH conjugate.

As used herein, the term 'long-acting hGH conjugate' refers to a conjugate in which a physiologically active peptide human growth hormone (hGH) is linked to an immunoglobulin Fc region and the physiological activity of which has an increased in vivo duration compared to a wild-type hGH. The term 'long-acting,' as used herein, means that the physiological activity has a longer duration than a wild-type hGH. As used herein, the term 'conjugate' refers to hGH that is coupled to an immunoglobulin Fc region.

As used herein, the term 'human growth hormone (hGH)' refers to a peptide hormone that stimulates growth, cell reproduction and regeneration in humans. The information on the sequence of hGH can be obtained from common database such as NCBI GenBank. In addition, the scope of hGH in the present invention includes a protein possessing an amino acid sequence having a sequence homology of 70% or higher, preferably 80% or higher, more preferably 90% or higher, even more preferably 95% or higher, and most preferably 98% or higher to an amino acid sequence of a wild-type human growth hormone, as long as it has a hGH activity. Also, as long as its biological activity is not significantly changed, any mutant derived from a wild-type hGH by substitution, deletion, or insertion of amino acid residues may be used in the present invention.

The hGH useful in the present invention may have an amino acid sequence of a wild-type hGH, its variant, its derivative, or fragments thereof.

As used herein, the term 'hGH variant' refers to a peptide having one or more amino acid sequences different from those of wild-type hGH while demonstrating the hGH activity. The hGH variant may be prepared by substitution, addition, deletion, or modification of some amino acids of a wild-type hGH or a combination thereof.

As used herein, the term 'hGH derivative' refers to a peptide having at least 80% amino acid sequence homology to a wild-type hGH and a hGH activity, in which some groups of the amino acid residues are chemically substituted (e.g., alpha-methylation, alpha-hydroxylation), deleted (e.g., deamination), or modified (e.g., N-methylation).

As used herein, the term 'hGH fragment' refers to a peptide in which one or more amino acids are added or deleted at the N-terminal or the C-terminal of hGH while retaining a hGH activity, and the added amino acids may not be a naturally occurring amino acids (for example, D-type amino acid).

In addition, hGH used in the present invention may be obtained from a native or recombinant protein. Preferably, it is the recombinant hGH prepared by using *E. coli* as a host cell, but is not limited thereto.

As used herein, the term 'immunoglobulin Fc region' refers to a part of immunoglobulin excluding the variable regions of the heavy chain and light chain, the heavy-chain constant region 1 ($CH_1$) and the light-chain constant region 1 ($CL_1$) of the immunoglobulin. The immunoglobulin Fc region may be the heavy-chain constant region 2 ($CH_2$) and the heavy-chain constant region 3 ($CH_3$) of an immunoglobulin, and may further comprise a hinge region at the heavy-chain constant region, but is not limited thereto. Also, the immunoglobulin Fc region of the present invention may be an extended Fc region that comprises a portion or full of the heavy-chain constant region ($CH_1$) and/or the light-chain constant region 1 ($CL_1$) except for the variable regions of the heavy chain and light chain of immunoglobulin, as long as it has substantially the same or improved effect than a wild-type protein. Also, the immunoglobulin Fc region may be a fragment wherein a considerably long portion of the amino acid sequence corresponding to $CH_2$ and/or $CH_3$ is deleted. That is, the immunoglobulin Fc region of the present invention may comprise 1) a $CH_1$ domain, a $CH_2$ domain, a $CH_3$ domain and a $CH_4$ domain, 2) a $CH_1$ domain and a $CH_2$ domain, 3) a $CH_1$ domain and a $CH_3$ domain, 4) a $CH_2$ domain and a $CH_3$ domain, 5) a combination of one or more domains and an immunoglobulin hinge region (or a portion of the hinge region), and 6) a dimer of a domain of the heavy-chain constant regions and a light-chain constant region, but is not limited thereto.

The immunoglobulin Fc region of the present invention comprises a native amino acid sequence and an amino acid sequence derivative (mutant) thereof. The amino acid sequence derivative refers to the sequence having different sequence from the native sequence by deletion, insertion, non-conservative or conservative substitution of one or more amino acid residues of the native amino acid sequence, or combinations thereof. For example, in IgG Fc, amino acid residues at positions 214 to 238, 297 to 299, 318 to 322, or 327 to 331 which are known to be important for protein binding may be suitable targets for modification.

Also, other types of derivatives may be used including the derivatives wherein a region capable of forming a disulfide bond is deleted, few amino acid residues at the N-terminal of a native Fc are eliminated, or a methionine residue is added at the N-terminal of a native Fc. Further, in order to eliminate a function of effector, a complement-binding site, for example C1q-binding site or antibody dependent cell mediated cytotoxicity (ADCC) site, may be deleted. Techniques for preparing such sequence derivatives of the immunoglobulin Fc region are disclosed in WO 97/34631 and WO 96/32478.

Substitution of amino acids in proteins and peptides, which do not change the overall protein activity, are known in the art (H. Neurath, R. L. Hill, The Proteins, Academic Press, New York, 1979). The most-commonly occurring exchanges are Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu and Asp/Gly, in both directions. In some cases, the Fc region may be modified by phosphorylation, sulfation, acrylation, glycosylation, methylation, farnesylation, acetylation, amidation, and the like. The aforementioned Fc derivatives demonstrate the same biological activity as the Fc region of the present invention, and they have an enhanced structural stability against heat, pH, and the like.

In addition, these Fc regions may be obtained from native proteins isolated from humans and other animals including cows, goats, swine, mice, rabbits, hamsters, rats and guinea pigs, or may be recombinants obtained from transformed animal cells or microorganisms or derivatives thereof. Here, the method of obtaining Fc regions from native immunoglobulin may include isolating the whole immunoglobulins from human or animal bodies and treating them with a protease. When papain is used for digesting immunoglobulins, they are cleaved into Fab and Fc regions, and when pepsin is used, the immunoglobulin is cleaved into pF'c and F(ab)2. These fragments may be separated using a size exclusion chromatography to isolate Fc or pF'c. Preferably, a human-derived Fc region is a recombinant immunoglobulin Fc region obtained from a microorganism.

In addition, the immunoglobulin Fc region of the present invention may be in a form of native sugar chains, longer sugar chains than native form, shorter sugar chains than native form, or a deglycosylated form. The extension or removal of the immunoglobulin Fc sugar chains may be done by using common methods in the art including chemical methods, enzymatic methods, and gene engineering method using a microorganism. The removal of sugar chains from an immunoglobulin Fc region results in a sharp decrease in its binding affinity to C1q of the first complement component C1 and thus a antibody-dependent cell-mediated cytotoxicity or complement-dependent cytotoxicity is reduced or removed, and the occurrence of unnecessary immune responses in vivo can be avoided. In this regard, a deglycosylated or aglycosylated immunoglobulin Fc region is more preferable form as a drug carrier for the object of the present invention.

As used herein, the term 'deglycosylation' refers to removing sugar moieties from Fc region using an enzyme, and the term 'aglycosylation' refers to the unglycosylated state of Fc region which is produced from a prokaryote, preferably E. coli.

Meanwhile, the immunoglobulin Fc region may be derived from humans or other animals including cows, goats, pigs, mice, rabbits, hamsters, rats and guinea pigs, and preferably from humans.

In addition, the immunoglobulin Fc region may be those derived from IgG, IgA, IgD, IgE and IgM, or those prepared by a combination or hybrid thereof. Preferably, it is derived from IgG or IgM, which are among the most abundant proteins in human blood, and most preferably from IgG, which is known to enhance a half-life of ligand-binding protein.

Meanwhile, the term 'combination', as used herein, refers to a conjugation between a polypeptide encoding single-chain immunoglobulin Fc regions of the same origin and a single-chain polypeptide of different origins when forming a dimer or multimer. That is, a dimer or multimer can be formed from two or more fragments selected from the group consisting of IgG Fc, IgA Fc, IgM Fc, IgD Fc, and IgE Fc fragments.

The term 'hybrid', as used herein, refers to when a single-chain immunoglobulin Fc region possesses sequences encoding two or more immunoglobulin Fc fragments of different origins. In the present invention, various types of hybrids may be used. That is, a hybrid of domains may be composed of one to four domains selected from the group consisting of $CH_1$, $CH_2$, $CH_3$ and $CH_4$ of IgG Fc, IgM Fc, IgA Fc, IgE Fc and IgD Fc, and may comprise a hinge region.

Meanwhile, IgG may also be divided into subclasses, IgG1, IgG2, IgG3 and IgG4, and a combination or hybrid thereof is also possible in the present invention, preferably IgG2 and IgG4 subclasses, and most preferably Fc region of IgG4 that lacks effector function such as complement-dependent cytotoxicity.

In other words, the most preferable immunoglobulin Fc region of conjugate in the present invention is a human IgG4-derived non-glycosylated Fc region. The human-derived Fc region acts as an antigen in human body and thus it is preferable than a non-human derived Fc region which can cause undesirable immune responses such as production of new antibody against antigen.

The long-acting hGH conjugate of the present invention can be prepared by combining a hGH prepared from a native or recombinant form by any method and an immunoglobulin Fc region prepared by treating a wild-type IgG with certain protease or produced from a transformed cell by using a recombination technique.

As a combining method used for this purpose, the conjugate can be prepared by cross-linking a hGH and a immunoglobulin Fc region using a non-peptidyl polymer or produced as a fusion protein wherein hGH and immunoglobulin Fc region are linked using a recombination technique. That is, the conjugate can be produced in a form where a human growth hormone and immunoglobulin Fc are linked through a non-peptidyl linker, or in a form of fusion protein of hGH and immunoglobulin Fc. The fusion protein comprises a form where a hGH and an immunoglobulin Fc are combined through a peptidyl linker, but is not limited thereto.

The term 'non-peptidyl polymer', as used herein, refers to a biocompatible polymer in which two or more repeating units are combined and the repeating units are connected to each other by any conjugation, but not a peptide bonding. In the present invention, the non-peptidyl polymer may be used interchangeably with the non-peptidyl linker.

The non-peptidyl polymer used for cross-linking may be selected from the group consisting of a biodegradable polymer including polyethylene glycol, polypropylene glycol, ethylene glycol-propylene glycol copolymer, polyoxyethylated polyol, polyvinyl alcohol, polysaccharide, dextran, polyvinyl ethyl ether, polylactic acid (PLA) or polylactic-glycolic acid (PLGA), a lipid polymer, chitin, hyaluronic acid, and a combination thereof, and preferably polyethylene glycol (PEG), but is not limited thereto. In addition, their derivatives that are already known in the art and derivatives that can be easily prepared by a method known in the art may be included in the scope of the present invention.

For preparing the long-acting hGH conjugate of the present invention, references such as Korean Patent No. 0725315 are disclosed in the present invention as a cited reference. Those skilled in the art can produce the long-acting hGH conjugates of the present invention according to the reference, but is not limited thereto.

As used herein, the term 'liquid formulation of highly concentrated long-acting hGH conjugate' refers to a liquid formulation which comprises long-acting human growth hormone conjugates at a high concentration. In the present invention, the liquid formulation of long-acting hGH conjugate may comprise a pharmaceutically effective amount of long-acting hGH conjugate. In general, the pharmaceutically effective amount of hGH corresponds to about 1 to 3 mg in a single-use vial, but is not limited thereto.

In addition, the concentration of long-acting hGH conjugate comprised in the liquid formulation of the present invention ranges from 1 to 150 mg/mL, preferably from 15 to 100 mg/mL, and more preferably from 20 to 100 mg/mL, but is not limited thereto.

The liquid formulation of highly concentrated long-acting hGH conjugate of the present invention contains a high concentration of hGH conjugate per unit of formulation, compared to the pre-existing liquid formulation with low concentration and thus it can carry a stable form of hGH into the body and store a high concentration of hGH conjugates without causing protein precipitation unlike the pre-existing liquid formulation. Especially, even when the formulation contains 20 to 100 mg/mL of hGH conjugates, it still keeps the stability of the conjugate.

The liquid formulation of highly concentrated long-acting hGH conjugate comprises a pharmaceutically effective amount of long-acting hGH conjugate, and an albumin-free stabilizer.

As used herein, the term 'stabilizer' refers to a substance that allows the long-acting hGH conjugate to be stored stably. Preferably, the stabilizer comprises a buffer, a non-ionic surfactant, a sugar alcohol and sodium chloride as an isotonic agent. With regard to the proteins like long-acting hGH conjugates, the storage stability is important for ensuring dose accuracy and suppressing the formation of potential antigens against long-acting hGH conjugate.

As used herein, the term 'buffer' refers to a solution that is comprised in the stabilizer of the present invention and works to maintain a stable pH level of the liquid formulation preventing a sharp change in pH to keep the activity of the long-acting hGH conjugate stable. The buffer may include an alkaline salt (sodium, potassium phosphate, or monobasic salts or dibasic salts thereof), sodium citrate/citric acid, sodium acetate/acetic acid, as well as any other pharmaceutically acceptable pH buffer that is known in the art, and a combination thereof. For the objects of the present invention, the buffer is preferably an acetate buffer, but is not limited thereto. The concentration of acetate salts that constitute sodium acetate buffer is preferably in a range of 5 to 100 mM and more preferably in a range of 10 to 50 mM, but is not limited thereto. Preferably, the pH of the buffer is in a range of 4.0 to 7.0, more preferably in a range of 5.0 to 6.0, and most preferably in a range of 5.2 to 6.0. In one example of the present invention, it was confirmed that the sodium acetate buffer with pH of 5.6 is suitable for maintaining a stability of long-acting hGH conjugates having various concentration (Table 5).

As used herein, the term 'sugar alcohol' refers to a hydrogenated carbohydrate that is comprised in the liquid formulation of the present invention and works to improve the stability of the long-acting hGH conjugate. The concentration of sugar alcohol used in the present invention is preferably in a range of 1 to 10% (w/v) of a total volume of the formulation, and more preferably in a range of 5 to 10% (w/v), but is not limited thereto. The sugar alcohol used in the present invention may be one or more sugar alcohols selected from the group consisting of mannitol and sorbitol, preferably mannitol, but is not limited thereto.

As used herein, the term 'isotonic agent' refers to an agent that maintains an appropriate osmotic pressure when a highly concentrated solution of the long-acting hGH conjugate is being injected into the body. The isotonic agent may have an effect of further stabilizing the long-acting hGH conjugate in solution. Example of the isotonic agent is a water-soluble inorganic salt and preferably sodium chloride. The concentration of sodium chloride used in the present invention is preferably in a range of 5 to 200 mM, but is not limited thereto. Also, depending on the type and amount of the substances comprised in the formulation, the amount of isotonic agent included can be adjusted such that the liquid formulation comprising all of the ingredients becomes isotonic.

As used herein, the term 'non-ionic surfactant' refers to a substance that reduces a surface tension of the protein solution to prevent the absorption or aggregation of proteins onto a hydrophobic surface. Preferable examples of the non-ionic surfactant that can be used in the present invention include polysorbate-type and poloxamer-type non-ionic surfactants and a combination thereof, with preference for a polysorbate-type non-ionic surfactant. Examples of the polysorbate-type non-ionic surfactants are polysorbate 20, polysorbate 40, polysorbate 60 and polysorbate 80, and among them polysorbate 80 is preferred, but is not limited thereto.

Meanwhile, it is not appropriate to add the non-ionic surfactant at a high concentration to the liquid formulation, since a high concentration of non-ionic surfactants cause interference effects when protein is analyzed to determine protein concentration or stability through analytic methods such as UV-spectrometric method or isoelectric focusing (IEF) and thus make it hard to determine protein stability accurately. Therefore, the liquid formulation of the present invention may comprise the non-ionic surfactant preferably at a concentration of 0.1% (w/v) or less, more preferably in a range of 0.001 to 0.1% (w/v), and even more preferably in a range of 0.001 to 0.05% (w/v), but it not limited thereto. In one example of the present invention, it was confirmed that when a concentration of polysorbate 80 was 0.2% (w/v) in a stabilizer comprising acetate buffer, sugar alcohol, sodium chloride as an isotonic agent, and polysorbate 80, it induced precipitation of long-acting hGH conjugate after 2 weeks (Table 8).

In addition, it is preferred that the stabilizer of the present invention does not contain albumin.

Since a human serum albumin that can be used as a protein stabilizer is produced from human serum, there is a risk of being contaminated with pathogenic viruses derived from human. In addition, gelatin or bovine serum albumin may cause diseases or may induce an allergic response in some patients. The albumin-free stabilizer of the present invention proteins does not contain heterologous proteins such as serum albumins derived from human or animal or purified gelatin, and thus there is no risk of viral infection.

Preferably, the stabilizer of the present invention may further comprise sugars, polyhydric alcohols or neutral amino acids.

Preferable examples of the sugars and sugars in polyhydric alcohols that can be further included in the formulation to increase the storage stability of the long-acting hGH conjugate are monosaccharides such as mannose, glucose, fucose and xylose, and polysaccharides such as lactose, maltose, sucrose, raffinose and dextran. Preferable examples of polyalcohols include propylene glycol, low-molecular weight polyethylene glycol, glycerol, low-molecular weight polypropylene glycol, and a combination thereof.

In addition, the liquid formulation of the present invention may further comprise other ingredients or materials that are known in the art selectively in addition to the above-described buffer, isotonic agent, sugar alcohols, and non-ionic surfactants, unless they do not diminish the effect of the present invention.

Specifically, the liquid formulation of the present invention may further comprise a preservative.

As used herein, 'preservative' refers to a substance that substantially reduces a bacterial contamination in the formulation. Especially, it is comprised in the formulation to facilitate the production of formulation for multiple dosing. Examples of preservatives include octadecyldimethyl-benzyl ammonium chloride, hexamethonium chloride, benzalkonium chloride (mixture of alkylbenzyldimethylammonium chloride which has a long alkyl chain), and benzethonium chloride. Other types of preservatives include aromatic alcohols such as phenol alcohol, butyl alcohol, and benzyl alcohol; alkyl paraben such as methylparaben or propylparaben; catechol; resorcinol; cyclohexanol; 3-pentanol; and m-cresol, but are not limited thereto. The preservative in the liquid formulation of the present invention is preferably benzyl alcohol or m-cresol, but is not limited thereto. The concentration of the preservative is preferably in a range of 1 to 10 mg/mL.

In one example of the present invention, the stability of immunoglobulin Fc region was examined at different pH and buffer. In case of pH, the immunoglobulin Fc region was stable in pH of 5.6 to 6.0, and at pH 5.6 the stability was even higher (Example 2 and Table 1). Among sodium citrate, sodium acetate, and histidine buffers, the stability was higher in sodium acetate buffer (Example 3 and Table 2). Based on these results, the liquid formulation comprising a long-acting hGH conjugate at a high concentration of 20 mg/mL or more, buffer, sodium chloride as an isotonic agent, mannitol as alcohol, and polysorbate 80 as surfactant was prepared. When sodium acetate was used as a buffer, the conjugate was not precipitated even after 2 weeks. Also, compared to a control group, the stability of the conjugate was higher than the control group (Example 4). Furthermore, the effect of concentration of sugar alcohols and surfactants comprised in the liquid formulation on long-acting hGH conjugate was examined. Then it was determined that the conjugate was stable in 5% to 10% mannitol, and was not precipitated in 0.2% (w/v) or lower concentration of polysorbate 80 (Example 5). Also, it was examined whether addition of preservative to the liquid formulation of the present invention will have an effect on the stability of long-acting hGH conjugate. The results demonstrate that the stability of conjugate was similar to a control group even when preservative such as benzyl alcohol or cresol is added. Therefore, it was confirmed that the present liquid formulation may further comprise preservative if repeated dosing is needed (Example 6).

As another embodiment, the present invention provides a method for preparing the liquid formulation of highly concentrated long-acting human growth hormone conjugate. The method of the present invention can prepare a stable liquid formulation of highly concentrated long-acting hGH conjugate, which comprises a long-acting hGH conjugate, and an albumin-free stabilizer, said stabilizer comprising the buffer, non-ionic surfactant, sugar alcohol and sodium chloride as an isotonic agent.

The long-acting hGH conjugate, liquid formulation, buffer, sugar alcohol, isotonic agent and non-ionic surfactant are the same as described above.

The method for preparing the liquid formulation of highly concentrated long-acting hGH conjugate may comprise the step of mixing the long-acting hGH conjugate with a stabilizer comprising buffer, non-ionic surfactant, sugar alcohol and sodium chloride as an isotonic agent. More specifically, the method may comprise the step of (a) producing a long-acting hGH conjugate or preparing the produced long-acting hGH conjugate; and (b) mixing the long-acting hGH conjugate prepared in the step (a) with the stabilizer comprising the buffer, non-ionic surfactant, sugar alcohol and sodium chloride as an isotonic agent, but is not limited thereto.

In addition, while mixing the long-acting hGH conjugate with the stabilizer in step (b) of the method, a preservative may be further added, but is not limited thereto.

When the liquid formulation prepared by the method of the present invention comprises a preservative, it can also used for multiple dosing.

Figure 1:
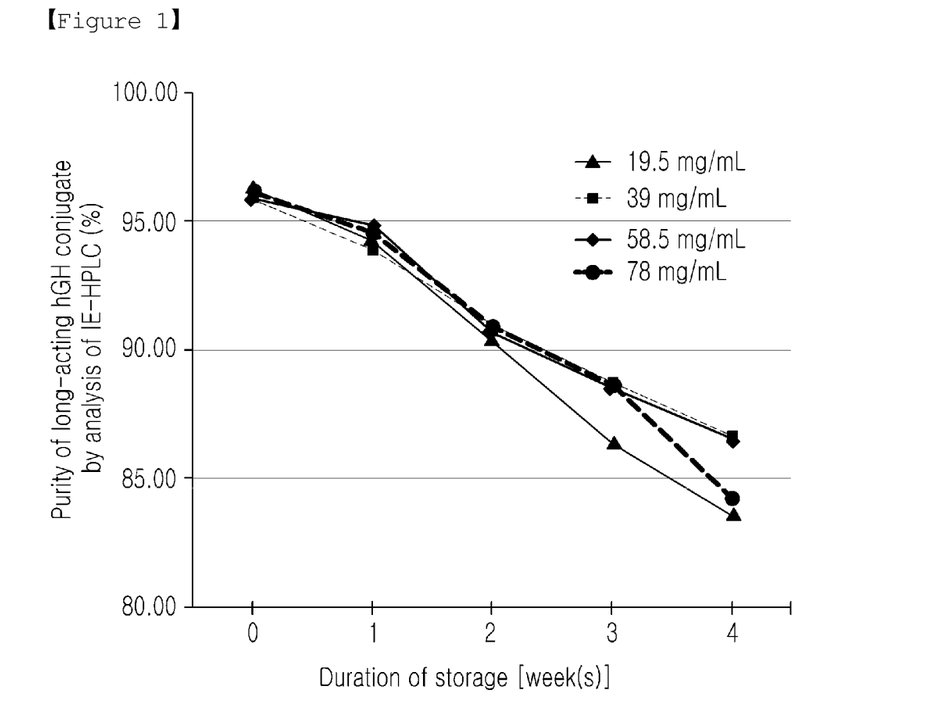
FIG. 1 demonstrates the results of an accelerated stability test of a liquid formulation of long-acting hGH conjugate comprising 20 mM sodium acetate buffer (pH 5.6), 150 mM sodium chloride, 5% mannitol and 0.005% polysorbate 80 during the storage thereof, according to the concentration of long-acting hGH conjugate, showing the IE-HPLC chromatogram for analyzing sample stability. It demonstrates that liquid formulations of long-acting hGH conjugate at a low concentration and high concentration retain similar level of stability.
Figure 2:
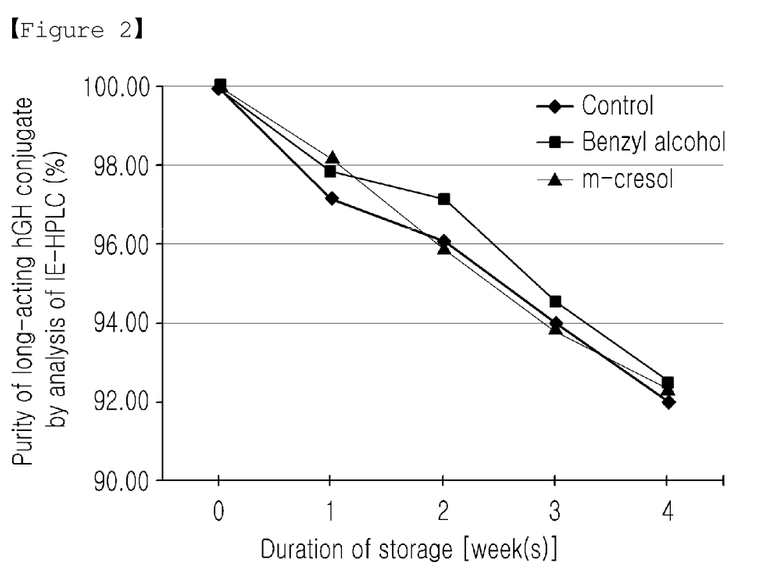
FIG. 2 demonstrates the results of an accelerated stability test of a liquid formulation of highly concentrated long-acting hGH conjugate further comprising 9 mg/mL benzyl alcohol or 3 mg/mL m-cresol in addition to 20 mM sodium acetate (pH 5.6), 150 mM sodium chloride, 5% mannitol and 0.005% polysorbate 80 during the storage thereof, according to the concentration of long-acting hGH conjugate, showing the IE-HPLC chromatogram for sample stability analysis. It demonstrates that the liquid formulations of highly concentrated long-acting hGH conjugate that are added with preservative such as benzyl alcohol or m-cresol retain a similar stability as those without preservatives (control).

According to the examples of the present invention, a stabilizer comprising sodium acetate buffer, sodium chloride as isotonic agent, mannitol as sugar alcohol, and polysorbate 80 as surfactant does not cause precipitation of the conjugate even when a high concentration of the long-acting hGH conjugate is added keeping its stability (Examples 1 to 5). That is, long-acting hGH conjugate at a high concentration of 20.0 mg/mL or more can be stable in the liquid formulation of the present invention without protein precipitation. Also, even when benzyl alcohol or m-cresol was added as a preservative to the liquid formulation, the stability is retained. Thus it was confirmed that if repeated dosing is needed, the preservative can be further added to the formulation (Example 6 and FIG. 2).

MODE FOR INVENTION

Hereinafter, the present invention is described in more detail with reference to Examples. However, these Examples are for illustrative purposes only, and the invention is not intended to be limited by these Examples.

Example 1: Preparation of Long-Acting hGH Conjugate

ALD-PEG-ALD, which is a polyethylene glycol with a molecular weight (MW) of about 3.4 kDa having an aldehyde group at both ends, was conjugated with hGH (MW 22 kDa), and then linked to the N-terminal of a human IgG4-derived aglycosylated Fc region (MW 50 kDa). Through this, the final product hGH-PEG-Fc conjugate which is a representative long-acting hGH conjugate of the present invention was prepared and purified.

Example 2: Analysis of the Stability of Immunoglobulin Fc Region at Different pH The stability of hGH polypeptide and immunoglobulin Fc region that constitute a long-acting hGH conjugate was evaluated under different conditions. The stability of immunoglobulin Fc region was compared at different pH in a liquid formulation which comprises buffer, sodium chloride, mannitol, and polysorbate 80.

Each of compositions of Table 1 was used as a buffer for immunoglobulin Fc region, which was then stored in the buffer at 40° C. for 4 weeks, and the stability of immunoglobulin was analyzed by using ion exchange chromatography (IE-HPLC). In Table 2, IE-HPLC (%) indicates the residual purity of the immunoglobulin Fc region in comparison with initial purity, represented by (Area %/Start Area %) %.

TABLE 1

| | Protein Concentration | Buffer | Isotonic agent | Sugar Alcohol | Surfactant |
|---|---|---|---|---|---|
| #1 | 19.5 mg/mL | 20 mM Sodium citrate (pH 4.8) | 150 mM Sodium chloride | 5% Mannitol | 0.005% Polysorbate 80 |
| #2 | 19.5 mg/mL | 20 mM Sodium citrate (pH 5.0) | 150 mM Sodium chloride | 5% Mannitol | 0.005% Polysorbate 80 |
| #3 | 19.5 mg/mL | 20 mM Sodium citrate (pH 5.2) | 150 mM Sodium chloride | 5% Mannitol | 0.005% Polysorbate 80 |
| #4 | 19.5 mg/mL | 20 mM Sodium citrate (pH 5.4) | 150 mM Sodium chloride | 5% Mannitol | 0.005% Polysorbate 80 |
| #5 | 19.5 mg/mL | 20 mM Sodium citrate (pH 5.6) | 150 mM Sodium chloride | 5% Mannitol | 0.005% Polysorbate 80 |
| #6 | 19.5 mg/mL | 20 mM Sodium citrate (pH 5.8) | 150 mM Sodium chloride | 5% Mannitol | 0.005% Polysorbate 80 |
| #7 | 19.5 mg/mL | 20 mM Sodium citrate (pH 6.0) | 150 mM Sodium chloride | 5% Mannitol | 0.005% Polysorbate 80 |

TABLE 2

| | IE-HPLC (%) | | | | |
|---|---|---|---|---|---|
| | Start | 1 week | 2 weeks | 3 weeks | 4 weeks |
| #1 | N/A | N/A | N/A | N/A | N/A |
| #2 | N/A | N/A | N/A | N/A | N/A |
| #3 | N/A | N/A | N/A | N/A | N/A |
| #4 | 100.0 | 89.8 | 81.8 | 71.4 | N/A |
| #5 | 100.0 | 91.3 | 83.3 | 77.1 | 67.9 |
| #6 | 100.0 | 91.2 | 83.1 | 76.3 | 66.8 |
| #7 | 100.0 | 91.2 | 82.6 | 75.5 | 65.6 |

*N/A: data unavailable due to precipitation by aggregation

As shown in Table 2, IE-HPLC (%) was 67.9% at pH 5.6 (#5) after 4 weeks, showing the highest stability of immunoglobulin Fc region. Also, at pH 4.8 to 5.2 (#1 to #3), the protein precipitation was induced from the start, so its stability could not be analyzed. and at pH 5.4 (#4), the precipitation occurred after 3 weeks.

Example 3: Analysis of the Stability of Immunoglobulin in Relation to Buffer Based on commercially available formulations of hGH, the stability of immunoglobulin Fc region was compared in different buffer including acetate, citrate, and histidine which are commonly used as buffer.

Each of compositions of Table 3 was used as buffer for immunoglobulin Fc region, which was then stored for 3 weeks at 40° C., and the stability of immunoglobulin Fc region was analyzed by using ion exchange chromatography. In Table 4, IE-HPLC (%) indicates the residual purity of the immunoglobulin Fc region in comparison with initial purity, represented by (Area %/Start Area %) %.

TABLE 3

| | Protein Concentration | Buffer | Isotonic Agent | Sugar Alcohol | Surfactant |
|---|---|---|---|---|---|
| #1 | 19.5 mg/mL | 20 mM Sodium citrate (pH 5.6) | 150 mM Sodium chloride | 5% Mannitol | 0.005% Polysorbate 80 |
| #2 | 19.5 mg/mL | 20 mM Sodium acetate (pH 5.6) | 150 mM Sodium chloride | 5% Mannitol | 0.005% Polysorbate 80 |
| #3 | 19.5 mg/mL | 20 mM Histidine (pH 5.6) | 150 mM Sodium chloride | 5% Mannitol | 0.005% Polysorbate 80 |

TABLE 4

| | IE-HPLC (%) | | | |
|---|---|---|---|---|
| | Start | 1 week | 2 weeks | 3 weeks |
| #1 | 100.0 | 87.3 | 76.2 | 67.8 |
| #2 | 100.0 | 88.9 | 77.6 | 68.2 |
| #3 | 100.0 | 86.7 | 74.6 | 63.3 |

As shown in Table 4, when sodium acetate of pH 5.6 (#2) was used as buffer, the residual purity of the immunoglobulin Fc region was 88.9% (1 week), 77.6% (2 weeks), and 68.2% (3 weeks).

These results suggest that when sodium acetate (#2) was used as buffer, the stability of immunoglobulin Fc region was higher than when sodium citrate (#1) and histidine (#3) were used.

Example 4: Analysis of the Stability of Long-Acting hGH Conjugate in Relation to Protein Concentration and Buffer Using the buffers examined in Example 3, the stability of highly concentrated long-acting hGH conjugate was compared. Each of compositions of Table 5 was used as a liquid formulation for highly concentrated long-acting hGH conjugate, which was then stored at 25° C. for 4 weeks, and the stability of the conjugate was analyzed by using ion exchange chromatography and size exclusion chromatography (SE-HPLC).

In Table 6, IE-HPLC (%) and SE-HPLC (%) indicate the purity of highly concentrated long-acting hGH conjugate at the point of analysis.

TABLE 5

| | Protein Concentration | Buffer | Isotonic Agent | Sugar Alcohol | Surfactant |
|---|---|---|---|---|---|
| Control | 19.5 mg/mL | 20 mM Sodium citrate (pH 5.2) | 150 mM Sodium chloride | 5% Mannitol | 0.005% Polysorbate 80 |
| #1 | 39.0 mg/mL | 20 mM Sodium citrate (pH 5.2) | 150 mM Sodium chloride | 5% Mannitol | 0.005% Polysorbate 80 |
| #2 | 39.0 mg/mL | 20 mM Sodium citrate (pH 5.6) | 150 mM Sodium chloride | 5% Mannitol | 0.005% Polysorbate 80 |
| #3 | 39.0 mg/mL | 20 mM Sodium acetate (pH 5.6) | 150 mM Sodium chloride | 5% Mannitol | 0.005% Polysorbate 80 |

TABLE 5-continued

| | Protein Concentration | Buffer | Isotonic Agent | Sugar Alcohol | Surfactant |
|---|---|---|---|---|---|
| #4 | 5.85 mg/mL | 20 mM Sodium citrate (pH 5.2) | 150 mM Sodium chloride | 5% Mannitol | 0.005% Polysorbate 80 |
| #5 | 5.85 mg/mL | 20 mM Sodium citrate (pH 5.6) | 150 mM Sodium chloride | 5% Mannitol | 0.005% Polysorbate 80 |
| #6 | 5.85 mg/mL | 20 mM Sodium acetate (pH 5.6) | 150 mM Sodium chloride | 5% Mannitol | 0.005% Polysorbate 80 |
| #7 | 78.0 mg/mL | 20 mM Sodium citrate (pH 5.2) | 150 mM Sodium chloride | 5% Mannitol | 0.005% Polysorbate 80 |
| #8 | 78.0 mg/mL | 20 mM Sodium citrate (pH 5.6) | 150 mM Sodium chloride | 5% Mannitol | 0.005% Polysorbate 80 |
| #9 | 78.0 mg/mL | 20 mM Sodium acetate (pH 5.6) | 150 mM Sodium chloride | 5% Mannitol | 0.005% Polysorbate 80 |

TABLE 6

| | IE-HPLC (%) | | | | | SE-HPLC (%) | | | | |
|---|---|---|---|---|---|---|---|---|---|---|
| | Start | 1 week | 2 weeks | 3 weeks | 4 weeks | Start | 1 week | 2 weeks | 3 weeks | 4 weeks |
| Control | 96.20 | 94.21 | 90.34 | 86.39 | 83.64 | 97.27 | 96.73 | 96.59 | 96.11 | 96.09 |
| # 1 | 96.01 | 94.76 | 90.52 | 88.26 | 85.77 | 97.30 | 97.02 | 96.77 | 96.24 | 95.98 |
| # 2 | 96.04 | 92.88 | 90.16 | 85.77 | 83.17 | 97.21 | 96.71 | 96.56 | 96.16 | 95.86 |
| # 3 | 95.99 | 93.91 | 90.90 | 88.75 | 86.62 | 97.27 | 96.73 | 96.77 | 96.29 | 96.09 |
| # 4 | 96.03 | 94.71 | 90.63 | 88.54 | 85.71 | 97.22 | 97.08 | 96.58 | 96.20 | 95.96 |
| # 5 | 95.99 | 92.60 | 90.12 | 85.66 | 83.15 | 97.19 | 97.10 | 96.39 | 96.00 | 95.67 |
| # 6 | 96.03 | 94.72 | 90.85 | 88.56 | 86.61 | 97.15 | 96.69 | 96.62 | 96.21 | 96.02 |
| # 7 | 96.15 | 94.53 | 90.60 | 88.50 | 82.53 | 97.21 | 96.77 | 96.61 | 96.18 | 95.93 |
| # 8 | 96.14 | 92.57 | 90.11 | 85.56 | 82.81 | 97.20 | 96.74 | 96.40 | 95.95 | 95.64 |
| # 9 | 96.17 | 94.53 | 90.91 | 88.66 | 84.22 | 97.20 | 96.76 | 96.61 | 96.21 | 96.02 |

As shown in Table 6, when 20 mM sodium acetate with pH 5.6 (#3, #6, #9) was used as buffer, after 4 weeks of storage, the stability of highly concentrated long-acting hGH conjugate was higher than when 20 mM sodium citrate of pH 5.6 was used (#2, #5, #8).

Also, with the protein concentration as high as 39.0 mg/mL to 78.0 mg/mL, when sodium citrate of pH 5.2 (#1, #4, #7) or sodium citrate of pH 5.6 (#2, #5, #8) were used as buffer, the protein started to precipitate after 2 weeks of storage and the precipitation level was increased after 3 weeks of storage.

Example 5: Analysis of the Stability of Highly Concentrated Long-Acting hGH Conjugate in Relation to the Concentrations of Sugar Alcohol and Surfactant Using the liquid formulation examined in Example 4 (comprising 20 mM sodium acetate with pH 5.6, 150 mM sodium chloride, 5% (w/v) mannitol, 0.005% (w/v) polysorbate 80), the stability of highly concentrated long-acting hGH conjugate was examined at different concentrations of sugar alcohol and surfactant. Here, the concentration of sugar alcohol and surfactant was selected to be within a maximum allowable range set by the available formulation or suggested by approval institution.

Each of compositions of Table 7 was used as a liquid formulation for highly concentrated long-acting hGH conjugate, which was then stored at 25° C. for 4 weeks, and the stability of conjugate was analyzed by using ion exchange chromatography and size exclusion chromatography.

In Table 8, IE-HPLC (%) and SE-HPLC (%) indicate the purity of highly concentrated long-acting hGH conjugate at the time of analysis.

TABLE 7

| | Protein Concentration | Buffer | Isotonic Agent | Sugar Alcohol | Surfactant |
|---|---|---|---|---|---|
| Control-1 | 39.0 mg/mL | 20 mM Sodium acetate (pH 5.6) | 150 mM Sodium chloride | 5% Mannitol | 0.005% Polysorbate 80 |
| #1 | 39.0 mg/mL | 20 mM Sodium acetate (pH 5.6) | 150 mM Sodium chloride | 10% Mannitol | 0.005% Polysorbate 80 |
| #2 | 39.0 mg/mL | 20 mM Sodium acetate (pH 5.6) | 150 mM Sodium chloride | 5% Mannitol | 0.2% Polysorbate 80 |

TABLE 7-continued

| | Protein Concentration | Buffer | Isotonic Agent | Sugar Alcohol | Surfactant |
|---|---|---|---|---|---|
| #3 | 39.0 mg/mL | 20 mM Sodium acetate (pH 5.6) | 150 mM Sodium chloride | 10% Mannitol | 0.2% Polysorbate 80 |
| Control-2 | 78.0 mg/mL | 20 mM Sodium acetate (pH 5.6) | 150 mM Sodium chloride | 5% Mannitol | 0.005% Polysorbate 80 |
| #4 | 78.0 mg/mL | 20 mM Sodium acetate (pH 5.6) | 150 mM Sodium chloride | 10% Mannitol | 0.005% Polysorbate 80 |
| #5 | 78.0 mg/mL | 20 mM Sodium acetate (pH 5.6) | 150 mM Sodium chloride | 5% Mannitol | 0.2% Polysorbate 80 |
| #6 | 78.0 mg/mL | 20 mM Sodium acetate (pH 5.6) | 150 mM Sodium chloride | 10% Mannitol | 0.2% Polysorbate 80 |

TABLE 8

| | IE-HPLC (%) | | | | | SE-HPLC (%) | | | | |
|---|---|---|---|---|---|---|---|---|---|---|
| | Start | 1 week | 2 weeks | 3 weeks | 4 weeks | Start | 1 week | 2 weeks | 3 weeks | 4 weeks |
| Control-1 | 96.15 | 95.06 | 91.77 | 89.30 | 86.42 | 97.22 | 96.96 | 96.87 | 96.71 | 96.50 |
| #1 | 96.12 | 95.04 | 91.68 | 89.11 | 86.19 | 97.22 | 96.96 | 96.77 | 96.15 | 96.09 |
| #2 | 96.12 | 95.04 | 91.64 | 89.14 | 86.31 | 97.30 | 96.94 | 96.78 | 96.12 | 95.96 |
| #3 | 96.12 | 94.88 | 90.47 | 87.36 | 84.10 | 97.19 | 96.96 | 96.69 | 95.96 | 95.82 |
| Control-2 | 96.15 | 95.08 | 91.76 | 89.33 | 86.40 | 97.25 | 96.90 | 96.86 | 96.69 | 96.42 |
| #4 | 96.12 | 95.04 | 91.65 | 89.10 | 86.20 | 97.26 | 96.93 | 96.77 | 96.17 | 96.14 |
| #5 | 96.07 | 95.01 | 91.61 | 89.07 | 86.31 | 97.20 | 96.94 | 96.76 | 96.21 | 95.97 |
| #6 | 96.10 | 94.95 | 90.45 | 87.31 | 84.10 | 97.18 | 96.95 | 96.62 | 96.04 | 95.84 |

As shown in Table 8, when 20 mM sodium acetate with pH 5.6 was used along with mannitol and polysorbate 80, the stability of highly concentrated long-acting hGH conjugate was highest in control-1 and control-2. Also, when the concentration of polysorbate 80 was 0.2% (w/v), the test groups #2, #3, #5 and #6 showed protein precipitation at any concentration after 2 weeks.

Example 6: Analysis of the Stability of Highly Concentrated Long-Acting hGH Conjugate Formulation in Relation to a Preservative Using the liquid formulation identified in Example 5 (comprising 20 mM sodium acetate with pH 5.6, 150 mM sodium chloride, 5% (w/v) mannitol, 0.005% (w/v) polysorbate 80), the stability of highly concentrated long-acting hGH conjugate was examined in relation to preservative. Here, as a representative preservative, benzyl alcohol and m-cresol were used.

Specifically, each of compositions of Table 9 was used as a liquid formulation for highly concentrated long-acting hGH conjugate, which was then stored at 25° C. for 4 weeks, and the stability of the formulation was examined by using ion exchange chromatography and size exclusion chromatography.

In Table 10, IE-HPLC (%) and SE-HPLC (%) indicate the purity of highly concentrated long-acting hGH conjugate at the point of early comparison.

TABLE 9

| | Protein Concentration | Buffer | Isotonic Agent | Sugar Alcohol | Surfactant | Preservative |
|---|---|---|---|---|---|---|
| Control | 39.0 mg/mL | 20 mM Sodium acetate (pH 5.6) | 150 mM Sodium chloride | 5% Mannitol | 0.005% Polysorbate 80 | — |

TABLE 9-continued

| | Protein Concentration | Buffer | Isotonic Agent | Sugar Alcohol | Surfactant | Preservative |
|---|---|---|---|---|---|---|
| #1 | 39.0 mg/mL | 20 mM Sodium acetate (pH 5.6) | 150 mM Sodium chloride | 5% Mannitol | 0.005% Polysorbate 80 | 9 mg/mL Benzyl alcohol |
| #2 | 39.0 mg/mL | 20 mM Sodium acetate (pH 5.6) | 150 mM Sodium chloride | 5% Mannitol | 0.005% Polysorbate 80 | 3 mg/mL m-cresol |

TABLE 10

| | IE-HPLC (%) | | | | | SE-HPLC (%) | | | | |
|---|---|---|---|---|---|---|---|---|---|---|
| | Start | 1 week | 2 weeks | 3 weeks | 4 weeks | Start | 1 week | 2 weeks | 3 weeks | 4 weeks |
| Control | 100.00 | 97.16 | 96.09 | 94.04 | 92.03 | 100.00 | 98.97 | 99.20 | 98.94 | 98.79 |
| #1 | 100.00 | 97.88 | 97.18 | 94.57 | 92.52 | 100.00 | 99.91 | 101.15 | 100.49 | 100.25 |
| #2 | 100.00 | 98.19 | 95.92 | 93.87 | 92.37 | 100.00 | 100.11 | 100.06 | 100.30 | 99.90 |

As shown in Table 10, when 9 mg/mL benzyl alcohol or 3 mg/mL m-cresol was used as preservative, the stability of formulation was similar to that of control group.

This result demonstrates that even when the formulation comprising highly concentrated long-acting hGH conjugate of the present invention further comprises a preservative, the stability of hGH is not affected. Thus the formulation of the present invention that comprises preservative can be applied for repeated dosing.

It will be apparent to those skilled in the art that various modifications and changes may be made without departing from the scope and spirit of the invention. Therefore, it should be understood that the above embodiment is not limitative, but illustrative in all aspects. The scope of the invention is defined by the appended claims rather than by the description preceding them, and therefore all changes and modifications that fall within metes and bounds of the claims, or equivalents of such metes and bounds are therefore intended to be embraced by the claims.

The invention claimed is:

1. A stable liquid formulation of highly concentrated long-acting human growth hormone (hGH) conjugate, comprising a pharmaceutically effective amount of the long-acting human growth hormone conjugate in which hGH is linked to an immunoglobulin Fc region, a preservative, and an albumin-free stabilizer, said stabilizer consisting essentially of an acetate buffer, a non-ionic surfactant, a sugar alcohol and sodium chloride,
wherein the preservative is an m-cresol or benzyl alcohol,
wherein a concentration of the long-acting hGH conjugate ranges from 58.5 to 100 mg/mL based on the total amount of the liquid formulation, and a content of the preservative ranges from 1 to 10 mg/mL based on the total amount of the liquid formulation and
wherein the stable liquid formulation retains at least 68.2% of purity of the immunoglobulin Fc region after a storage at 40° C. for 3 weeks and at least 84.22% of purity of the immunoglobulin Fc region after a storage at 25° C. for 4 weeks, wherein the purity of the immunoglobulin Fc region is represented by the following formula:

(Area %/Start Area %)×100, wherein the Start Area % is the volume of pure immunoglobulin Fc region determined by ion exchange HPLC at time zero, and the Area % is the volume of the pure immunoglobulin Fc region determined by ion exchange HPLC at the 3 week or 4 week, both ion exchange HPLC being carried out under same conditions.

2. The stable liquid formulation according to claim 1, wherein the sugar alcohol is selected from the group consisting of mannitol, sorbitol and a combination thereof.

3. The stable liquid formulation according to claim 1, wherein the non-ionic surfactant is polysorbate 80.

4. The stable liquid formulation according to claim 1, wherein the stabilizer further comprises one or more ingredients selected from the group consisting of a sugar, a polyhydric alcohol and an amino acid.

5. The stable liquid formulation according to claim 1, wherein the hGH has the same amino acid sequence as a wild-type hGH.

6. The stable liquid formulation according to claim 1, wherein the immunoglobulin Fc region is an Fc region of an immunoglobulin isotype selected from the group consisting of IgG, IgA, IgD, IgE and IgM.

7. The stable liquid formulation according to claim 1, wherein the immunoglobulin Fc region is a hybrid of domains of different immunoglobulin isotypes selected from the group consisting of IgG, IgA, IgD, IgE, and IgM.

8. The stable liquid formulation according to claim 6, wherein the immunoglobulin Fc region is a dimer or multimer composed of two or more single-chain immunoglobulin consisting of domains of a single immunoglobulin isotype.

9. The stable liquid formulation according to claim 6, wherein the immunoglobulin Fc region is an IgG4 Fc region.

10. The stable liquid formulation according to claim 9, wherein the immunoglobulin Fc region is an aglycosylated human IgG4 Fc region.

11. The stable liquid formulation according to claim 1, wherein the long-acting human growth hormone conjugate is a conjugate in which the hGH is linked with the immunoglobulin Fc region via a non-peptidyl polymer, or by using a genetic recombination technique.

12. The stable liquid formulation according to claim 11, wherein the non-peptidyl polymer is selected from the group consisting of biodegradable polymers such as polyethylene glycol, polypropylene glycol, copolymers of ethylene glycol and propylene glycol, polyoxyethylated polyols, polyvinyl alcohol, polysaccharides, dextran, polyvinyl ethyl ether, polylactic acid, and polylactic-glycolic acid, lipid polymers, chitins, hyaluronic acid, and a combination thereof.

13. The stable liquid formulation according to claim 12, wherein the non-peptidyl polymer is a polyethylene glycol.

14. A stable liquid formulation of highly concentrated long-acting human growth hormone (hGH) conjugate, comprising a long-acting human growth hormone conjugate in which hGH is linked to an immunoglobulin fragment via polyethylene glycol, a preservative, and an albumin-free stabilizer, said stabilizer consisting essentially of an acetate buffer, a mannitol, a polysorbate 80, and sodium chloride,
wherein the preservative is an m-cresol or benzyl alcohol,
wherein a concentration of the long-acting hGH conjugate ranges from 58.5 to 100 mg/mL based on the total amount of the liquid formulation,
wherein a content of the mannitol ranges from 1 to 10% (w/v) of the total volume of the liquid formulation,
wherein the liquid formulation has a pH ranges from 5.0 to 6.0,
wherein a content of the sodium chloride ranges from 5 to 200 mM,
wherein a content of the polysorbate 80 ranges from 0.001 to 0.05% (w/v) of the total volume of the liquid formulation, and
wherein a content of the preservative ranges from 1 to 10 mg/mL based on the total amount of the liquid formulation.

15. A method for preparing the stable liquid formulation of claim 1, comprising mixing a long-acting hGH conjugate with a stabilizer and a preservative, said stabilizer consisting essentially of a buffer, a sugar alcohol, a non-ionic surfactant and a sodium chloride as an isotonic agent, wherein the buffer is an acetate buffer and wherein a concentration of the long-acting hGH conjugate ranges from 58.5 to 100 mg/mL based on the total amount of the liquid formulation.

16. The stable liquid formulation according to claim 1, which is for a multiple dose formulation.

17. The stable liquid formulation according to claim 1, wherein a concentration of the long-acting human growth hormone conjugate ranges from 78 to 100 mg/mL.

18. A stable liquid formulation of highly concentrated long-acting human growth hormone (hGH) conjugate, comprising a long-acting human growth hormone conjugate in which hGH is linked to an immunoglobulin fragment via polyethylene glycol, a preservative, and an albumin-free stabilizer, said stabilizer comprising 20 mM acetate buffer, 5% (w/v) mannitol, 0.005% (w/v) polysorbate 80, and 150 mM sodium chloride, wherein the preservative is 3 mg/ml of m-cresol or 9 mg/ml of benzyl alcohol.

* * * * *